(12) United States Patent
Li et al.

(10) Patent No.: US 10,302,379 B1
(45) Date of Patent: May 28, 2019

(54) APPARATUS OF HEAT PIPE QUALITY DETECTION USING INFRARED THERMAL IMAGER AND METHOD THEREOF

(71) Applicant: Institute of Nuclear Energy Research, Atomic Energy Council, Executive Yuan, R.O.C., Taoyuan (TW)

(72) Inventors: Heng-Yi Li, New Taipei (TW); Tsair-Fuh Huang, Taoyuan (TW); How-Ming Lee, Taoyuan (TW); Po-Hsiu Kuo, Taoyuan (TW); Yu-Ren Chen, Changhua County (TW)

(73) Assignee: INSTITUTE OF NUCLEAR ENERGY RESEARCH, ATOMIC ENERGY COUNCIL, EXECUTIVE YUAN, R.O.C., Taoyuan (TW)

( * ) Notice: Subject to any disclaimer, the term of this patent is extended or adjusted under 35 U.S.C. 154(b) by 28 days.

(21) Appl. No.: 15/855,118

(22) Filed: Dec. 27, 2017

(51) Int. Cl.
| | |
|---|---|
| *F28F 19/00* | (2006.01) |
| *F28F 3/00* | (2006.01) |
| *F28F 99/00* | (2006.01) |
| *G01J 5/06* | (2006.01) |
| *G01J 5/02* | (2006.01) |
| *G01J 5/00* | (2006.01) |

(52) U.S. Cl.
CPC .............. *F28F 99/00* (2013.01); *G01J 5/025* (2013.01); *G01J 5/06* (2013.01); *F28F 2200/005* (2013.01); *F28F 2245/06* (2013.01); *F28F 2275/025* (2013.01); *G01J 2005/0077* (2013.01)

(58) Field of Classification Search
CPC ....... G01N 25/72; G01N 27/221; G01J 5/025; G01J 5/06; G01J 2005/0077; F28F 2200/005; F28F 2245/06; F28F 2275/025; F24F 11/02; F24D 19/1084
USPC ..................................................... 165/11.2
See application file for complete search history.

(56) References Cited

U.S. PATENT DOCUMENTS

| | | | | |
|---|---|---|---|---|
| 4,872,762 A | * | 10/1989 | Koshihara .............. | G01N 25/72 374/5 |
| 4,886,370 A | * | 12/1989 | Koshihara .............. | G01N 25/72 374/5 |
| 4,983,836 A | * | 1/1991 | Matoba .................. | G01N 25/72 250/330 |
| 4,988,210 A | * | 1/1991 | Koshihara .............. | G01N 25/72 250/341.6 |

* cited by examiner

*Primary Examiner* — Davis D Hwu
(74) *Attorney, Agent, or Firm* — Jackson IPG PLLC; Demian K. Jackson (57) ABSTRACT

An apparatus is provided for detecting the quality of a heat pipe. The apparatus has an infrared (IR) thermal imager bound with a data computing-and-analyzing program to detect thermal conductivity quality and vacuum quality of the heat pipe. An online overall detection is thus provided to quickly detect the quality of the heat pipe without damage for efficient quality control. Requirements of quality detection are met for mass production of heat pipes. The apparatus comprises the heat pipe to be tested; a tape adhered to a surface of the heat pipe; a fixed base for disposing the heat pipe; a heating device in an allocation space of the fixed base; the IR thermal imager located facing to the tape; a signal line connected to the IR thermal imager; and an electronic device connected to the IR thermal imager through the signal line.

10 Claims, 5 Drawing Sheets

APPARATUS OF HEAT PIPE QUALITY DETECTION USING INFRARED THERMAL IMAGER AND METHOD THEREOF

TECHNICAL FIELD OF THE INVENTION

The present invention relates to an apparatus and method for detecting the quality of a heat pipe; more particularly, to obtaining the apparatus having an infrared (IR) thermal imager bound with a data computing-and-analyzing program to detect thermal conductivity quality and vacuum quality of the heat pipe, where an online overall detection is thus provided to quickly detect the quality of the heat pipe without damage for efficient quality control and meeting requirements of quality detection for mass production of heat pipes.

DESCRIPTION OF THE RELATED ARTS

Heat pipe is a most common high-efficiency thermally conductive (not heat-dissipating) device used in modern electronic products for heat dissipation.

Some prior arts exist: A prior art discloses a method of detecting temperature of a heat pipe through an IR thermal image, which uses the IR thermal image to detecting the temperature of the heat pipe. Another prior art discloses a device of detecting temperature on degassing a heat pipe, which uses a temperature sensor to detect temperature. Another prior art discloses a detecting device for heat pipes, which uses a temperature sensor to detect performance of a heat pipe. Another prior art discloses a method and a device for detecting the vacuum degree of a heat pipe, which provides a vacuum environment and, after destructing a heat pipe, the vacuum degree is obtained through an analysis with calculation of changes in temperature, humidity and pressure. Another prior art, US patent No. 2008/0271463 A1, reveals a heat pipe measuring system, which installs a heater and a temperature sensor at an evaporating side of the heat pipe and installs a thermal-electric cooler (TEC) and another temperature sensor at a condensing side of the heat pipe for deciding the quality of the heat pipe by measuring temperature changes. Another prior art, US patent No. 2005/0220168 A1, reveals a measuring device for heat pipe, which heats up an evaporating section of a heat pipe and cools down a condensing section of the heat pipe for deciding thermal conductivity by measuring temperature changes of the two sections.

However, the above prior arts for detecting a heat pipe have the following disadvantages:

1. Temperature sensors have to be installed on the surface of the heat pipes. Each heat pipe has to be detected separately. It takes time and labor very much. Vacuum degree and thermal conductivity cannot be determined altogether.

2. In one of the above prior arts, a special film has to be covered on the surface of the heat pipe for detecting temperature through the IR thermal image. Although it saves time and labor, this special film is not easy to obtain so that cost increases. Vacuum degree and thermal conductivity still cannot be determined altogether.

3. In one of the above prior arts, a vacuum environment is required and the heat pipe has to be destructed for calculating vacuum degree by analyzing changes in temperature, humidity and pressure. Each heat pipe has to be detected separately. It consumes time and labor very much. Vacuum degree and thermal conductivity still cannot be determined altogether.

Consequently, the traditional heat pipe detection methods cannot meet the need for quality detection of the heat pipes under mass production.

Vacuum degree and thermal conductivity are important indicators for the quality of a heat pipe. The modern quality detection of the heat pipes under mass production is usually done through detection one by one under random sampling. Overall detection is not possible and time consumes or the heat pipe has to be destructed. Not to mention, the prior arts still cannot determine vacuum degree and thermal conductivity at the same time. Hence, the prior arts do not fulfill all users' requests on actual use.

SUMMARY OF THE INVENTION

The main purpose of the present invention is to provide an apparatus for detecting the quality of a heat pipe, where an IR thermal imager is bound with a data computing-and-analyzing program to detect thermal conductivity quality and vacuum quality of the heat pipe. An online overall detection is thus provided to quickly detect quality without damaging the heat pipe for efficient quality control. Requirements of quality detection are met for mass production of heat pipes.

To achieve the above purposes, the present invention is an apparatus of heat pipe quality detection using an IR thermal imager, comprising a heat pipe to be tested, a tape, a fixed base, a heating device, an IR thermal imager, a signal line and an electronic device, where the heat pipe has a closed cavity; a working fluid is filled in the closed cavity; the working fluid is a fluid continuously cycling and capable of changing between a liquid phase and a vapor phase in the closed cavity according to temperature; the heat pipe comprises a heated region, a uncondensed gas region and a saturated vapor region; the saturated vapor region is between the heated region and the uncondensed gas region; the tape is adhered on a surface of the heat pipe to be tested to improve measurement accuracy by compensating bad emissivity of the heat pipe; the fixed base comprises a fixed plate and a plurality of plate foots; the fixed plate is a plate body with a hole fitted with heat pipe penetrating through at center; the plate foots are located at periphery of the fixed plate; an allocation space is obtained with the fixed plate and the plate foot of the fixed base; an end of the heat pipe is deposed in the fixed base through the hole; the heating device is located in the allocation space of the fixed base and is corresponding to the hole; the heating device heats up the part of the heat pipe lower than the fixed plate which part penetrates through the hole with the end of the heat pipe; the heated region is thus obtained at the part of the heat pipe lower than the fixed plate; the saturated vapor region and the uncondensed gas region are obtained at the rest part of the heat pipe which rest part is located higher than the fixed plate; the IR thermal imager is located facing to the tape adhered on the surface of the heat pipe to be tested; the IR thermal imager detects temperature changes and temperature distribution of the heat pipe adhered with the tape to obtain and output an IR thermal image; the IR thermal image has data comprising a temperature ($T_{111}$) at an upper end of the saturated vapor region; a temperature ($T_{112}$) at a lower end of the saturated vapor region; a length ($L_1$) of the saturated vapor region; a length ($L_2$) of the uncondensed gas region; the signal line is connected to the IR thermal imager to receive and transmit the IR thermal image; the electronic device is connected to the IR thermal imager through the signal line; the electronic device comprises a display, a computer mainframe and an input module; the computer mainframe is connected to the display and the input module electrically; a heat-pipe quality detection program is installed inside the computer mainframe; the input module obtains a thermal conductivity quality standard (K1) and a vacuum quality standard (K2) both inputted by a user according to manufacture target and production experience; the heat-pipe quality detection program reads K1 and K2 and reads the IR thermal image outputted from the IR thermal imager through the signal line; the heat-pipe quality detection program differs a good-quality product from a poor-quality product by using a criterion of thermal conductivity quality and a criterion of vacuum quality; and, at last, the temperature distribution of the heat pipe and a detection result of thermal conductivity quality and vacuum quality are sent to be shown on the display.

The present invention further uses a method comprising steps of: (a) adhering the tape on a surface of the part of the heat pipe which part is located higher than the heated region, where the heat pipe is filled with the working fluid capable of changing between a vapor phase and a liquid phase according to temperature; (b) deposing the heat pipe at the fixed base, where the tape is located facing to the IR thermal imager and the heated region is located lower than the fixed plate of the fixed base; (c) by using the heating device, heating the part of the heat pipe which part is located lower than the fixed plate to obtain the heated region of the heat pipe which heated part is located lower than the fixed plate, where the saturated vapor region and the uncondensed gas region are obtained at the part of the heat pipe which part is located higher than the fixed plate; (d) using the IR thermal imager to obtain the IR thermal image, where the part of the heat pipe which part is adhered with the tape is detected and measured to obtain T111, T112, L1 and L2 from the IR thermal image; (e) inputting K1 and K2 by the user according to the manufacture target and the production experience; outputting T111, T112, L1 and L2 by using the IR thermal imager; and obtaining thermal conductivity quality and vacuum quality according to the criterion of thermal conductivity quality and the criterion of vacuum quality to differ the good-quality product from the poor-quality product; and (f) reading results of the temperature distribution, the thermal conductivity quality and the vacuum quality to be shown to the display. Accordingly, a novel apparatus of heat pipe quality detection using an IR thermal imager is obtained.

BRIEF DESCRIPTION OF THE DRAWINGS

The present invention will be better understood from the following detailed description of the preferred embodiment according to the present invention, taken in conjunction with the accompanying drawings, in which.

DESCRIPTION OF THE PREFERRED EMBODIMENT

The following description of the preferred embodiment is provided to understand the features and the structures of the present invention.

Please to FIG. 1-FIG. 5, which are a view showing a preferred embodiment according to the present invention; a flow view showing a heat-pipe quality detection program; a view showing regions of an IR thermal image; a flow view showing a method used by the present invention; and a view showing an IR thermal image of heat pipes. As shown in the figures, the present invention is an apparatus of heat pipe quality detection using an IR thermal imager. The apparatus shown in FIG. 1 comprises a heat pipe 1 to be tested, a tape 2, a fixed base 3, a heating device 4, an IR thermal imager 5, a signal line 6, a heat-pipe quality detection program 7 and an electronic device 8.

Figure 1:
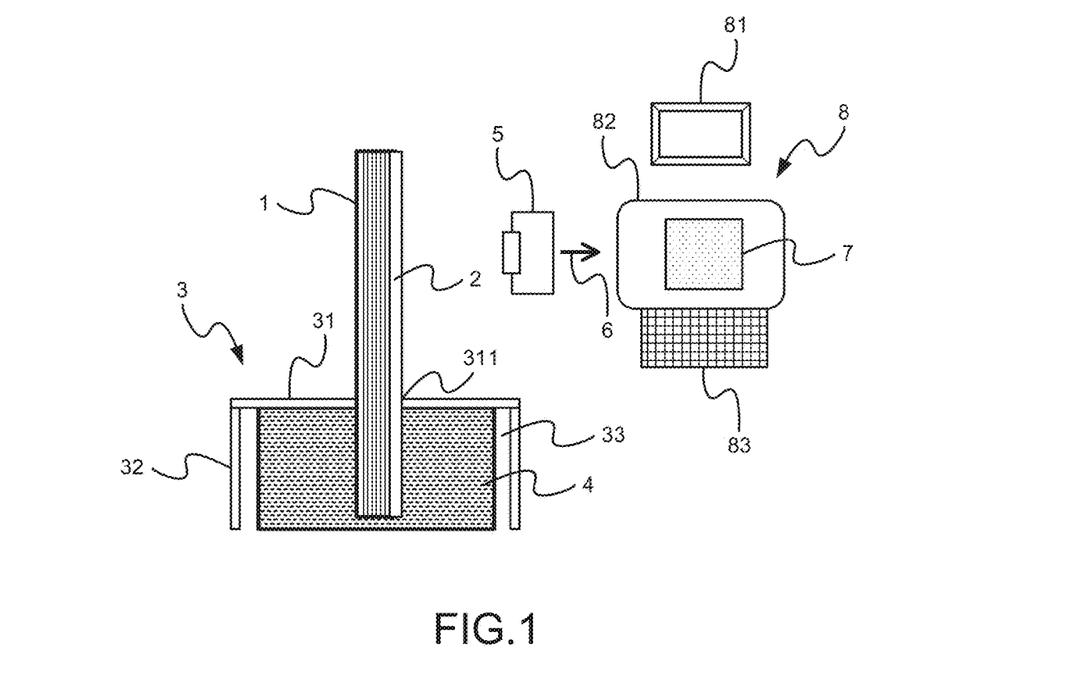
FIG. 1 is the view showing the preferred embodiment according to the present invention.

The heat pipe 1 to be tested has a closed cavity holding a working fluid. The working fluid is a fluid continuously cycling in the closed cavity and capable of changing between a liquid phase and a vapor phase according to temperature. Thus, heat transfer is achieved by quickly equalizing the surface temperature of the closed cavity. The heat pipe 1 to be tested comprises a heated region 10, an uncondensed gas region 12 and a saturated vapor region 11; and the saturated vapor region 11 is between the heated region 10 and the uncondensed gas region 12.

The tape 2 is adhered on a surface of the heat pipe 1 to be tested, which has an emissivity better than 0.8, a thickness smaller than 0.2 millimeters (mm), and a thermal tolerance of a temperature higher than 100 celsius degrees (° C.). Most polished metal surface has an emissivity worse than 0.1, which makes the IR thermal imager 5 hard to measure temperature. Therefore, the present invention has the tape 2 adhered on the surface of the heat pipe 1 to obtain good emissivity for detection, where the tape 2 can be a dark and opaque electrical insulation tape, a packaging tape or a document repair tape to compensate bad emissivity of the heat pipe for improving measurement accuracy.

The fixed base 3 comprises a fixed plate 31 and a plurality of plate foots 32. The fixed plate 31 is a plate body with a hole 311 fitted with heat pipe penetrating through at center. The plate foots 32 are set at periphery of the fixed plate 31. An allocation space 33 is formed in the fixed base 3 with the fixed plate 31 and the plate foots 32 while an end of the heat pipe 1 is set in the fixed base 3 by penetrating through the hole 311.

The heating device 4 is set in the allocation space 33 of the fixed base 3 and is located corresponding to the hole 311, where The heating device 4 heats up the part of the heat pipe 1 which part is located lower than the fixed plate 31 and penetrates the fixed plate 31 through the hole 311 with the end of the heat pipe 1. As a result, the heated region 10 is formed at the part of the heat pipe 1 which part is located lower than the fixed plate 31; and the saturated vapor region 11 and the uncondensed gas region 12 are formed at the rest part of the heat pipe 1 which rest part is located higher than the fixed plate 31. Therein, the heating device 4 can be a container holding hot water; a container holding hot oil; an electric furnace; a burning furnace; or a heating belt.

The IR thermal imager 5 is an instrument which turns the heat energy of IR radiation unseen by human eye into electric signals and shows the distribution of different temperatures through a variety of different colors for displaying a visible image of the entire temperature distribution. In the present invention, the IR thermal imager 5 is located facing to the tape 2 adhered on the surface of the heat pipe 1 to detect temperature changes and temperature distribution of the heat pipe 1 at the part adhered with the tape 2 for obtaining and outputting an IR thermal image. Therein, the IR thermal image has data comprising a temperature (T111) at an upper end of the saturated vapor region 11; a temperature (T112) at a lower end of the saturated vapor region 11; a length (L1) of the saturated vapor region 11; and a length (L2) of the uncondensed gas region 12.

The signal line 6 is connected to the IR thermal imager 5 for receiving and transmitting the IR thermal image.

Figure 2:
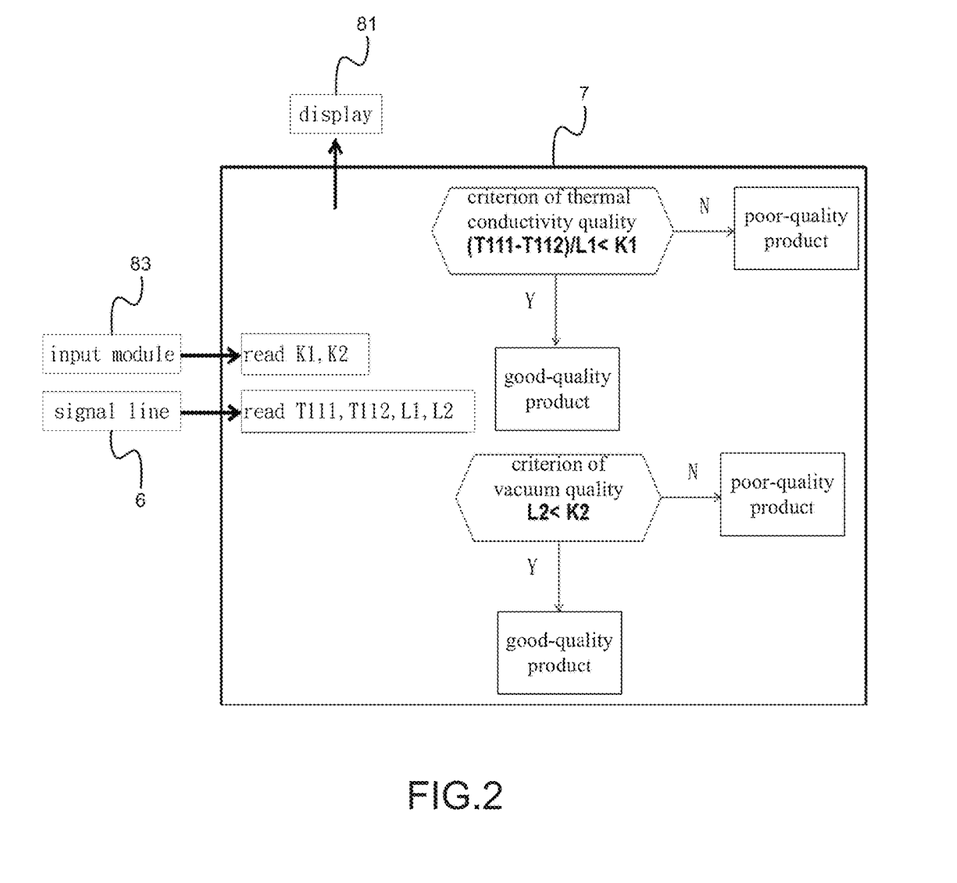
FIG. 2 is the flow diagram showing the heat-pipe quality detection program.

The electronic device 8 is connected to the IR thermal imager 5 through the signal line 6, which comprises a display 81, a computer mainframe 82 and an input module 83. The computer mainframe 82 is electrically connected to the display 81 and the input module 83; and is installed with a heat-pipe quality detection program. The flow view of the heat-pipe quality detection program is shown in FIG. 2. The input module 83 reads a thermal conductivity quality standard (K1) and a vacuum quality standard (K2) inputted by a user according to manufacture target and production experience; and reads the data comprising the temperature (T111) at the upper end of the saturated vapor region 11, the temperature (T112) at the lower end of the saturated vapor region 11, the length (L1) of the saturated vapor region 11 and the length (L2) of the uncondensed gas region 12 from the IR thermal image outputted by the IR thermal imager 5 through the signal line 6. Then, a good-quality product is differed from a poor-quality product by using a criterion of thermal conductivity quality and a criterion of vacuum quality. At last, the temperature distribution of the heat pipe 1 and a detection result of thermal conductivity quality and vacuum quality are sent to be shown on the display 81.

Figure 3:
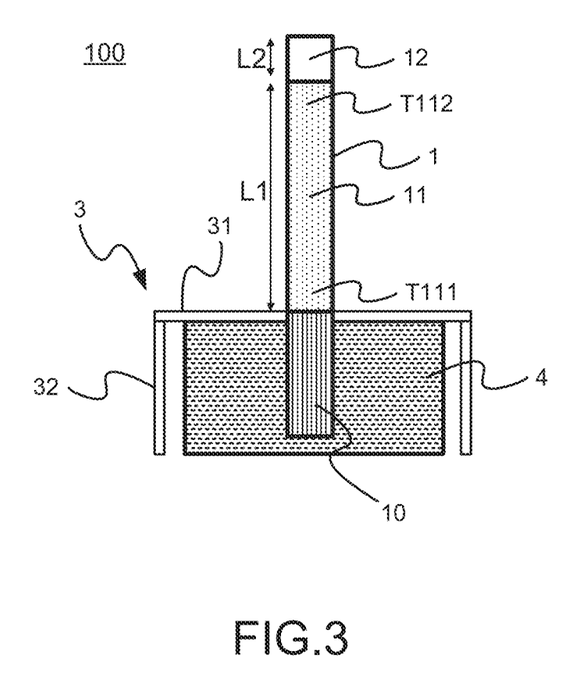
FIG. 3 is the view showing the regions of the infrared (IR) thermal image.

The meanings of T111, T112, L1 and L2 are shown in FIG. 3. In an environment 100 of a state-of-use, when the heated region 10 of the heat pipe 1 which region is located lower than the fixed plate 31 is heated for about 10~50 seconds, the surface temperature of the part of the heat pipe 1 which part is located higher than the fixed plate 31 will rise. However, if the vacuum quality of the heat pipe 1 is poor, uncondensed gas will be accumulated at an upper tip inside the heat pipe 1. Because the thermal conductivity coefficient of the uncondensed gas is low, the temperature does not rise too much. Thus, two regions comprising the saturated vapor region 11 and the uncondensed gas region 12 are formed, where the temperature of the saturated vapor region 11 is higher than that of the uncondensed gas region 12; and the temperature of the uncondensed gas region 12 is higher than that of the environment 100 of the state-of-use. T111 is the temperature of the part of the heat pipe 1 which part is located lower than the saturated vapor region 11; and T112 is the temperature of the part of the heat pipe 1 which part is located higher than the saturated vapor region 11. Because the part for T112 is located farther from heat source than that for T111, T112 is lower than T111. L1 is the length of the saturated vapor region 11; and L2 is the length of the uncondensed gas region 12. The user sets a thermal conductivity quality standard (K1) and a vacuum quality standard (K2) according to manufacture target and production experience. The criterion of thermal conductivity quality is (T111−T112)/L1<K1, where K1 is KT/L1 and KT is a temperature allowed to be reduced to. The good-quality product meets the criterion of thermal conductivity quality but the poor-quality product does not. The criterion of vacuum quality is L2<K2. The good-quality product meets the criterion of vacuum quality and the poor-quality product does not. At last, the temperature distribution of the heat pipe 1 and a detection result of thermal conductivity quality and vacuum quality are shown on the display 81.

Figure 4:
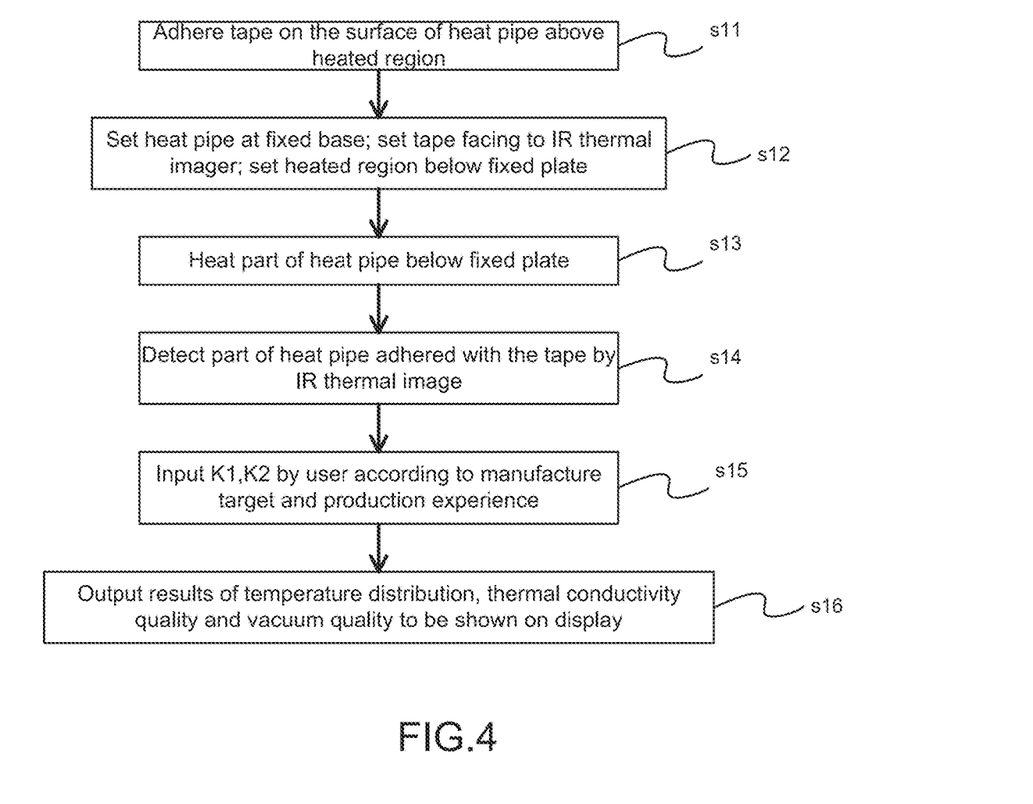
FIG. 4 is the flow diagram showing the method used by the present invention.

The method used by the apparatus according to the present invention is shown in FIG. 4. The method comprises the following steps:

(a) Step S11: The tape 2 is adhered on a surface of the part of the heat pipe 1 which part is located higher than the heated region 10 of the heat pipe 1, where the heat pipe 1 is filled with the working fluid capable of changing between a vapor phase and a liquid phase according to temperature.

(b) Step S12: The heat pipe 1 is set at the fixed base 3, where the tape 2 is set facing to the IR thermal imager 5 and the heated region 10 is set at a position lower than the fixed plate 31.

(c) Step S13: The part of the heat pipe 1 which part is located lower than the fixed plate 31 is heated by using the heating device 4 to obtain the heated region 10 of the heat pipe 1 which region is located lower than the fixed plate 31. The saturated vapor region 11 and the uncondensed gas region 12 are formed at the part of the heat pipe 1 which part is located higher than the fixed plate 31.

(d) Step S14: The IR thermal imager 5 is used to obtain the IR thermal image, where the part of the heat pipe 1 adhered with the tape 2 is detected and measured to obtain T111, T112, L1 and L2 from the IR thermal image.

(e) Step S15: K1 and K2 are inputted by the user according to the manufacture target and the production experience; T111, T112, L1 and L2 are outputted by using the IR thermal imager 5; and thermal conductivity quality and vacuum quality are obtained with the criterion of thermal conductivity quality and the criterion of vacuum quality for differing the good-quality product from the poor-quality product.

(f) Step S16: Results of the temperature distribution, the thermal conductivity quality and the vacuum quality are outputted to be shown on the display 81.

Figure 5:
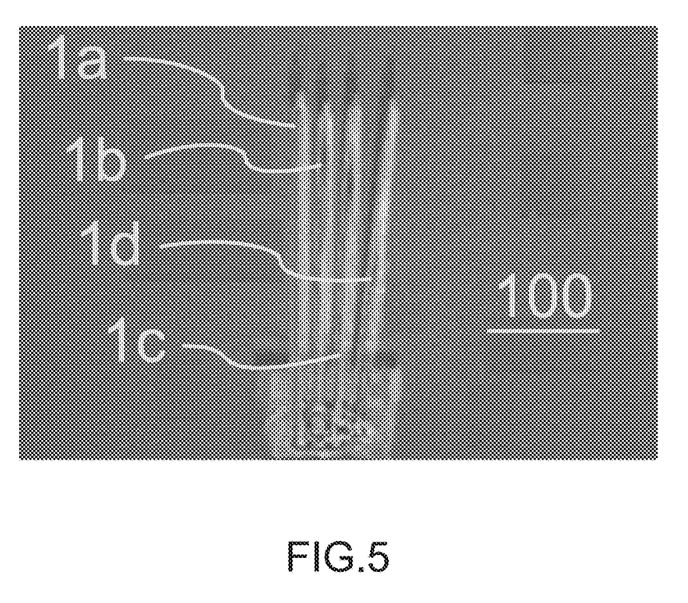
FIG. 5 is the view showing the IR thermal image of the heat pipes.

In another state-of-use, four heat pipes $1a,1b,1c,1d$ are filled with water used as a working fluid and are heated by hot water held in a glass for a time about 20 seconds, as shown in FIG. 5. Owing to having lighter density, uncondensed gas with a low temperature and poor thermal conductivity escapes first and floats on top inside the heat pipes 1. When being turned into saturated vapor, water obtains a higher temperature. Thus, two different regions 11,12 of the saturated vapor and the uncondensed gas are formed. The longer is the length (L2) of the uncondensed gas region 12, the more is the amount of uncondensed gas and the worse is the vacuum quality. In the figure, it is apparent that the temperature of the saturated vapor region 11 is higher than that of the uncondensed gas region 12; and the temperature of the uncondensed gas region 12 is higher than that of the environment 100 of the state-of-use. A fourth heat pipe $1d$ has a longer length (L2), so that it has poorer vacuum quality. The thermal conductivity quality and vacuum quality of a first heat pipe $1a$ are the best, whose KT=5° C., L1=250 mm, L2=1 mm, T111=72.5° C., T112=71.2° C., (T111−T112)/L1=5.2° C./m ('/m' means 'per meter').

Another state-of-use in addition to the above one can be formed except that the signal line 6, the heat-pipe quality detection program 7 and the electronic device 8 are omitted. Therein, the IR thermal image is directly outputted from the IR thermal imager 5; T111, T112, L1 and L2 are read from the IR thermal image by the IR thermal imager 5 or a computer to calculate (T111−T112)/L1; and the quality of the heat pipe is judged by a criterion of thermal conductivity quality and a criterion of vacuum quality.

Accordingly, the present invention proposes an apparatus and a method for detecting quality of a heat pipe by using an IR thermal image. More particularly, an IR thermal imager is used with coordination of a data calculating-and-analyzing program for detecting thermal conductivity quality and vacuum quality of the heat pipe. The present invention provides an online overall detection for quickly detecting the quality of the heat pipe without damage for efficient quality control. Requirements of quality detection are met for mass production of heat pipes.

To sum up, the present invention is an apparatus of heat pipe quality detection using an IR thermal imager, where an IR thermal imager is bound with a data computing-and-analyzing program to detect thermal conductivity quality and vacuum quality of a heat pipe; an online overall detection is thus provided to quickly detect quality without damaging the heat pipe for efficient quality control; and requirements of quality detection are met for mass production of heat pipes.

The preferred embodiment herein disclosed is not intended to unnecessarily limit the scope of the invention. Therefore, simple modifications or variations belonging to the equivalent of the scope of the claims and the instructions disclosed herein for a patent are all within the scope of the present invention.

What is claimed is:

1. An apparatus of heat pipe quality detection using an infrared (IR) thermal imager, comprising:
   a heat pipe to be tested,
      wherein said heat pipe has a closed cavity; a working fluid is filled in said closed cavity; said working fluid is a fluid continuously cycling and capable of changing between a liquid phase and a vapor phase in said closed cavity according to temperature; said heat pipe comprises a heated region, a uncondensed gas region and a saturated vapor region; and said saturated vapor region is between said heated region and said uncondensed gas region;
   a tape,
      wherein said tape is adhered on a surface of said heat pipe to be tested to improve measurement accuracy by compensating bad emissivity of said heat pipe;
   a fixed base,
      wherein said fixed base comprises a fixed plate and a plurality of plate foots; said fixed plate is a plate body with a hole fitted with heat pipe penetrating through at center; said plate foots are located at periphery of said fixed plate; an allocation space is obtained with said fixed plate and said plate foot of said fixed base; and an end of said heat pipe is deposed in said fixed base through said hole;
   a heating device,
      wherein said heating device is located in said allocation space of said fixed base and is corresponding to said hole; said heating device heats up the part of said heat pipe lower than said fixed plate which part penetrates through said hole with said end of said heat pipe; said heated region is thus obtained at said part of said heat pipe lower than said fixed plate; and said saturated vapor region and said uncondensed gas region are obtained at the rest part of said heat pipe which rest part is located higher than said fixed plate;
   an IR thermal imager,
      wherein said IR thermal imager is located facing to said tape adhered on said surface of said heat pipe to be tested; and said IR thermal imager detects temperature changes and temperature distribution of said heat pipe adhered with said tape to obtain and output an IR thermal image; and
      wherein said IR thermal image has data comprising a temperature (T111) at a first end of said saturated vapor region located next to said uncondensed gas region; a temperature (T112) at a second end of said saturated vapor region opposite to said first end; a length (L1) of said saturated vapor region; and a length (L2) of said uncondensed gas region;
   a signal line,
      wherein said signal line is connected to said IR thermal imager to receive and transmit said IR thermal image; and
   an electronic device,
      wherein said electronic device is connected to said IR thermal imager through said signal line; said electronic device comprises a display, a computer mainframe and an input module; said computer mainframe is connected to said display and said input module electrically; a heat-pipe quality detection program is installed inside said computer mainframe; said input module obtains a thermal conductivity quality standard (K1) and a vacuum quality standard (K2) both inputted by a user according to manufacture target and production experience; said heat-pipe quality detection program reads K1 and K2 and reads said IR thermal image outputted from said IR thermal imager through said signal line; said heat-pipe quality detection program differs a good-quality product from a poor-quality product by using a criterion of thermal conductivity quality and a criterion of vacuum quality; and, at last, said temperature distribution of said heat pipe and a detection result of thermal conductivity quality and vacuum quality are sent to be shown on said display.

2. The apparatus according to claim 1,
   wherein said tape compensates emissivity.

3. The apparatus according to claim 2,
   wherein said tape is selected from a group consisting of a dark and opaque electrical insulation tape, a packing tape and a document repair tape.

4. The apparatus according to claim 1,
   wherein said tape has an emissivity better than 0.8, a thickness smaller than 0.2 millimeters (mm), and a thermal tolerance of a temperature higher than 100 celsius degrees (° C.).

5. The apparatus according to claim 1,
   wherein said heating device is selected from a group consisting of a container holding hot water; a container holding hot oil; an electric furnace; a burning furnace; and a heating belt.

6. The apparatus according to claim 1,
   wherein said criterion of thermal conductivity quality is (T111−T112)/L1<K1;
   wherein K1 is KT/L1 and KT is a temperature allowed to be reduced to; and
   wherein said good-quality product meets said criterion of thermal conductivity quality but said poor-quality product does not.

7. The apparatus according to claim 1,
   wherein said criterion of vacuum quality is L2<K2; and
   wherein said good-quality product meets said criterion of vacuum quality but said poor-quality product does not.

8. The apparatus according to claim 1,
   wherein said signal line, said heat-pipe quality detection program and said electronic device are omitted; said IR thermal image is directly outputted from said IR thermal imager; and T111, T112, L1 and L2 are obtained from said IR thermal image by a device selected from a group consisting of said IR thermal imager and a computer to calculate (T111−T112)/L1 to obtain the quality of said heat pipe according to said criterion of thermal conductivity quality and said criterion of vacuum quality.

9. The apparatus according to claim 1, wherein said tape is adhered on a surface of the part of said heat pipe which part is located higher than said heated region.

10. The apparatus according to claim 1, wherein a method used by the apparatus comprises steps of:
  (a) adhering said tape on a surface of the part of said heat pipe which part is located higher than said heated region,
    wherein said heat pipe is filled with said working fluid capable of changing between a vapor phase and a liquid phase according to temperature;
  (b) deposing said heat pipe at said fixed base,
    wherein said tape is located facing to said IR thermal imager and said heated region is located lower than said fixed plate of said fixed base;
  (c) by using said heating device, heating the part of said heat pipe which part is located lower than said fixed plate to obtain said heated region of said heat pipe which heated part is located lower than said fixed plate,
    wherein said saturated vapor region and said uncondensed gas region are obtained at the part of said heat pipe which part is located higher than said fixed plate;
  (d) using said IR thermal imager to obtain said IR thermal image,
    wherein the part of said heat pipe which part is adhered with said tape is detected and measured to obtain T111, T112, L1 and L2 from said IR thermal image;
  (e) inputting K1 and K2 by said user according to said manufacture target and said production experience; outputting T111, T112, L1 and L2 by using said IR thermal imager; and obtaining thermal conductivity quality and vacuum quality according to said criterion of thermal conductivity quality and said criterion of vacuum quality to differ said good-quality product from said poor-quality product; and
  (f) reading results of said temperature distribution, said thermal conductivity quality and said vacuum quality to be shown to said display.

* * * * *